United States Patent [19]

Roth et al.

[11] Patent Number: 5,162,547

[45] Date of Patent: Nov. 10, 1992

[54] PROCESS FOR THE PREPARATION OF GLYCIDYL ETHERS

[75] Inventors: Martin Roth, Giffers; Heinz Wolleb, Marly; Marc-André Truffer, Antagnes/Ollon, all of Switzerland

[73] Assignee: Ciba-Geigy Corporation, Ardsley, N.Y.

[21] Appl. No.: 804,309

[22] Filed: Dec. 9, 1991

[30] Foreign Application Priority Data

Dec. 18, 1990 [CH] Switzerland .................. 4012/90

[51] Int. Cl.$^5$ .................. C07D 301/28; C07D 303/04
[52] U.S. Cl. .................. 549/516; 549/555; 549/560
[58] Field of Search .................. 549/516

[56] References Cited

U.S. PATENT DOCUMENTS

| 2,538,072 | 1/1951 | Zech .................. 260/348.6 |
| 3,686,358 | 8/1972 | Bertram .................. 260/830 |
| 4,474,944 | 10/1984 | Yasuda et al. .................. 549/516 |
| 4,549,008 | 10/1985 | Kenner et al. .................. 528/220 |

FOREIGN PATENT DOCUMENTS

| 827450 | 2/1960 | United Kingdom .................. 549/516 |
| 982151 | 2/1965 | United Kingdom . |
| 1453882 | 10/1976 | United Kingdom . |

OTHER PUBLICATIONS

J. Chem. Soc. Perkin Trans., I, 1984, pp. 1725–1732.

*Primary Examiner*—Joseph E. Evans

*Attorney, Agent, or Firm*—JoAnn Villamizar; William A. Teoli, Jr.

[57] ABSTRACT

An improved process for the preparation of glycidyl ethers of formula I

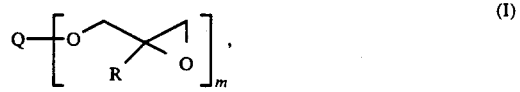

wherein Q is an aliphatic, cycloaliphatic or araliphatic radical of a valency m, R is —H or —CH$_3$, and m is an integer from 1 to 10, by reacting an alcohol of formula Q—(OH)$_m$ with m mol of an epihalohydrin of formula II

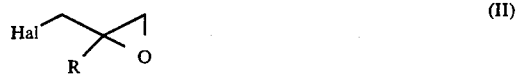

in the presence of a catalyst to the corresponding halohydrin ether, and dehydrohalogenating said halohydrin ether with an alkali metal hydroxide to give a compound of formula I, wherein Q, m and R are as defined above and Hal is halogen, which process comprises using as catalyst
a) tin difluoride or
b) a divalent tin halide in conjunction with a co-catalyst.

14 Claims, No Drawings

PROCESS FOR THE PREPARATION OF GLYCIDYL ETHERS

The present invention relates to an improved process for the preparation of aliphatic, cycloaliphatic or araliphatic glycidyl ethers by reacting an alcohol and an epihalohydrin in the presence of specific catalysts and subsequently dehydrohalogenating the resultant halohydrin ether with an alkali metal hydroxide.

Glycidyl ethers can be prepared by reacting alcohols and epihalohydrins using different kinds of catalysts, typically acid, basic or phase transfer catalysts. The acid catalysts used are so-called Lewis acids such as $AlCl_3$, $SbCl_5$, $SnCl_4$, $FeCl_3$, $ZnCl_2$ and $BF_3$, as disclosed, inter alia, in U.S. Pat. Nos. 2,538,072, 3,425,961 and 4,549,008, and in GB patents 827 450 and 982 151. The Lewis acids preferably used in these publications are boron trifluoride and, more particularly, tin(IV) tetrachloride. Finally, U.S. Pat. No. 3,686,358 postulates the use of divalent tin chloride for the preparation of dibromoneopentyl glycol diglycidyl ether.

It has now been found that the reaction of aliphatic, cycloaliphatic or araliphatic alcohols with epihalohydrins using specific catalyst systems derived from divalent tin halides proceeds much more selectively than with boron trifluoride or tin tetrachloride, and gives glycidyl ethers with lower chlorine and higher epoxy values.

Accordingly, the present invention relates to an improved process for the preparation of glycidyl ethers of formula I

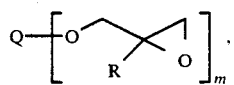

wherein Q is an aliphatic, cycloaliphatic or araliphatic radical of valency m, R is —H or —$CH_3$, and m is an integer from 1 to 10, by reacting an alcohol of formula Q—$(OH)_m$ with m mol of an epihalohydrin of formula II

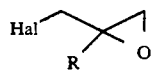

in the presence of a catalyst to the corresponding halohydrin ether, and dehydrohalogenating said halohydrin ether with an alkali metal hydroxide to give a compound of formula I, wherein Q, m and R are as defined above and Hal is halogen, which process comprises using as catalyst
a) tin difluoride or
b) a divalent tin halide in conjunction with a cocatalyst.

An aliphatic radical Q may be straight-chain or branched, saturated or unsaturated, and interrupted in the chain by one or more oxygen or sulfur atoms or contains one or more keto groups.

A cycloaliphatic radical Q may be saturated or unsaturated and contains one or more ring systems and may contain a keto group, which rings may be substituted by and/or linked through alkyl groups.

The aromatic moiety of an araliphatic radical Q may contain one or more rings or fused rings, such as phenyl, naphthyl, 4,4'-diphenyl, 4,4'-diphenylmethane, 4,4'-diphenyl(dimethyl)methane, 4,4'-diphenyloxide, 4,4'-diphenylketone or 4,4'-diphenylsulfone radicals which may themselves be substituted by $C_1$–$C_6$alkyl, $C_1$–$C_6$alkoxy or halogen. Araliphatic radicals are preferably aralkyl radicals in which the alkyl moiety may be unbranched or branched and they preferably contain 1 to 3 carbon atoms.

$C_1$–$C_6$Alkyl and $C_1$–$C_6$alkoxy may be straight-chain or branched and are typically methyl, ethyl, propyl, isopropyl, butyl, sec-butyl, tert-butyl, pentyl and hexyl and, respectively, methoxy, ethoxy, propoxy, isopropoxy, butoxy, tert-butoxy, pentoxy and hexoxy.

Halogen may be chloro, bromo or iodo, and is preferably bromo, and most preferably, chloro.

Q may be substituted by functional groups, provided that they do not inhibit the catalyst employed and do not undergo side-reactions with the epihalohydrins.

Q defined as alkyl (where m=1) is typically $C_1$–$C_{30}$alkyl, preferably $C_3$–$C_{20}$alkyl. Illustrative examples of such radicals are methyl, ethyl, n-propyl, isopropyl, n-butyl, sec-butyl, tert-butyl, pentyl, hexyl, heptyl, octyl, 2-ethylhexyl, nonyl, decyl, dodecyl, tetradecyl, hexadecyl, octadecyl, icosyl, docosyl, tetracosyl and pentacosyl.

Cycloalkyl radicals are typically cyclopentyl, cyclohexyl, cycloheptyl, cyclooctyl and cyclononyl, preferably cyclohexyl.

Exemplary of polyfunctional alcohols of formula Q—$(OH)_m$ are aliphatic, cycloaliphatic or araliphatic structural units such as butanediols, trimethylolpropane, bis(trimethylolpropane), pentaerythritol, cyclohexanediols, tricyclodecanedimethylol (e.g. tricyclo[5.2.1.0$^{2.6}$]decane-4,8-dimethanol) or perhydrobisphenol A.

Exemplary of alcohols of formula Q—$(OH)_m$ are: methanol, ethanol, propanol, isopropanol, butanol, sec-butanol, tert-butanol, pentanol, tert-pentanol, cclopentanol, hexanol, cyclohexanol, heptanol, octanol, decanol, dodecanol, tetradecanol, pentadecanol, hexadecanol, heptadecanol, octadecanol, benzylalkohol, diphenylmethanol, ethylene glycol, 1,2-propanediol, 1,3-propanediol, 1,4-butanediol, 1,2-butanediol, 2,3-butanediol, diethylene glycol, triethylene glycol, 1,5-pentanediol, 1,6-hexanediol, 2,4,6-hexanetriol, 2,2-dimethyl-1,3-propanediol, 2-ethyl-2-butyl-1,2-propanediol, 1,12-dihydroxyoctadecane, glycerol, erythritol, pentaerythritol, sorbitol, mannitol, inositol, 1,1,1-trimethylolpropane, 1,4-dimethylolbenzene, 4,4'-dimethyloldiphenyl, dimethylolxylenes, dimethylolnaphthalenes, polyether alcohols, such as diglycerol, and also bis(2,3-dihydroxypropyl ether), triglycerol, dipentaerythritol, dimethylolanisoles, beta-hydroxyethyl ethers of polyalcohols or phenols, such as diethylene glycol, polyethylene glycol or hydroquinone-bis(-beta-hydroxyethyl ether), bis(beta-hydroxyethyl ethers) of bisphenols, for example of 4,4'-dihydroxydiphenyldimethylmethane, as well as beta-hydroxyethyl ethers of glycerol, pentaerythritol, sorbitol or mannitol, condensates of alkylene oxides, such as ethylene oxide, propylene oxide, butylene oxide or isobutylene oxide, with the above-mentioned polyalcohols, and also hydroxy esters such as monoglycerides, for example monostearin, and ethylene glycol dilactate, monoesters of pentaerythritol, such as the monoacetate, and also halogenated alcohols, such as glycerol monochlorohydrin, 1,4-dichloro-2,3-dihydroxybutane, pentaerythritol monochlorides or dibromoneopentyl glycol, bis(4-hydroxycyclohexyl)methane, bis(4-hydroxycyclohexyl)dimethylmethane, 2,2-bis(4-hydroxycyclohexyl)propane, cyclohexane-1,1-dimethylol, 2,2,6,6-tetramethylolcyclohexanol, 2,2,5,5-tetramethylolcyclopentanol, 4-methyl-2,2,6,6-tetramethylolcyclohexanol, 2,2,6,6-tetramethylolcyclohexan-4-one, 1,2-, 1,3- and 1,4-dihydroxycyclohexane, 1,3-dihydroxycyclopentane, 4,4'-dihydroxydicyclohexyl, and mercaptoalcohols, such as 2-mercaptoethanol, alpha-monothioglycerol, 2,2',3,3'-tetrahydroxy dipropyl sulfide or 2,2'-dihydroxy diethyl sulfide.

A suitable epihalohydrin is typically epibromohydrin and, preferably, epichlorohydrin.

m is preferably an integer from 1 to 6.

In the formula $Q—(OH)_m$, Q is preferably a saturated aliphatic or cycloaliphatic radical.

The preferred saturated aliphatic radical in the definition of Q is alkyl.

Particularly preferred compounds of formula $Q—(OH)_m$ are primary or secondary monofunctional (m=1) or polyfunctional alcohols in which m is an integer from 2 to 6. Q is also very preferably a polyfunctional radical of up to 30 carbon atoms, in which case m is an integer from 2 to 6.

Suitable tin halides are tin dichloride, tin dibromide and, preferably, tin difluoride. These catalysts may be used within a wide concentration range without adversely affecting the reaction; but a concentration of 0.001 to 0.5 mol of catalyst per 1 mol of alcohol of formula $Q—(OH)_m$ is advantageous.

It is particularly preferred to use tin difluoride as sole catalyst in the practice of this invention.

Crown ethers or poly(alkylene oxide) dialkyl ethers may be used as co-catalysts. They are conveniently used in molar ratios to the tin halides. Illustrative examples of crown ethers are 18-crown-6, 15-crown-5, 12-crown-4, benzo-18-crown-6, benzo-15-crown-5, dibenzo-18-crown-6, dibenzo-24-crown 8 and dicyclohexano-18-crown-6. Illustrative examples of poly(alkylene oxide) dialkyl ethers are polyethylene glycol 400 dimethyl ether, polyethylene glycol 500 dimethyl ether and polyethylene glycol 1000 dimethyl ether.

The reaction of the compounds of formula $Q—(OH)_m$ with the epihalohydrins to give the halohydrin ethers is conveniently carried out without a solvent; but it may also be carried out in the presence of an inert organic solvent. Suitable organic solvents are typically halogenated hydrocarbons such as methylene chloride, chloroform, 1,2-dichloroethane, 1,1,1-trichloroethane, 1,2,2-trichloroethylene, 1,4-dichloropropane and chlorobenzene, also toluene, xylene, hexane, cyclohexane, heptane, octane, and esters, such as ethyl acetate and butyl acetate, ethers such as diethyl ether and diisopropyl ether, dioxane and tetrahydrofuran. Mixtures of the above solvents in any proportions can also be used. The amount of solvent or solvent mixture can vary to any degree. It is conveniently so chosen that the concentration of the reactants is in the range from 10 to 70%.

The epihalohydrin is conveniently added in an amount from 0.8 to 1.3 mol of epihalohydrin per hydroxyl group according to the formula $Q—(OH)_m$, but preferably in stoichiometric amounts or in a slight excess, for example an excess of up to 10%, based on the molar amount of epihalohydrin.

The reaction of the alcohol with the epihalohydrin may be carried out in the temperature range from 0° C. to the reflux temperature of the reaction mixture, preferably from 80° to 150° C. The overall reaction times vary, depending on the alcohol, from 30 minutes to 24 hours.

The adduct (halohydrin ether) of the epihalohydrin and the alcohol is preferably not isolated and is dehydrohalogenated direct. When carrying out the process of this invention the order in which the components is added is not essential. Possible process variants are: The alcohol is charged to the reactor with the catalyst and heated to the required reaction temperature. The epihalohydrin is then added over an appropriate period of time such that the temperature remains within a suitable range. Then the reaction is allowed to continue until analysis of the reaction mixture (gas chromatography, epoxide titration, chlorine determination or HPLC) shows the desired conversion to the corresponding halohydrin ether. Alternatively, all components, i.e. the alcohol, the epihalohydrin and the catalyst, are charged to the reactor and heated to the required temperature and further reacted until the desired conversion to the epihalohydrin ether.

The further process steps are identical in the above process variants. Any excess of epihalohydrin can be removed from the reaction mixture by distillation before the dehydrohalogenation. At this stage of the process it is also possible to separate the bulk of the tin halide or catalyst system by filtration and to reuse it.

The amount of catalyst so recovered will depend on the solubility of the catalyst in the reaction medium, but in the case of tin difluoride can be more than 90% in favourable circumstances. In some cases the yield of recovered catalyst can be increased by addition of an inert organic solvent.

The dehydrohalogenation of the halohydrin ether to the glycidyl ether can be carried out by the known conventional methods for using tin tetrachloride or boron trifluoride catalysts with an alkali metal hydroxide as base, with the elimination of alkali metal halide. The theoretically required stoichiometric amount may also be more or less than this amount in order to obtain the optimum low chlorine values of the final product. Usually amounts of 0.80 to 1.30 mol of alkali metal hydroxide per hydroxyl group and a temperature range from 30° to 60° C. are preferred. The use of an inert organic solvent is expedient if the viscosity of the reaction mixture is too high.

In some cases the glycidylation is best carried out by removing the water as an azeotrope in the presence of an alkali metal hydroxide. The alkali metal hydroxide is preferably added under reduced pressure during the azeotropic removal of water. In this manner, water which acts as solvent for the alkali metal hydroxide and water which is formed during the reaction is removed from the reaction mixture continuously.

The salt formed during the reaction, typically sodium chloride, can either be washed out or removed by filtration or centrifugation. Excess epichlorohydrin may be removed by vacuum distillation.

Compared with prior art processes, the improved process of this invention has a number of advantages, such as enhanced selectivity resulting in lower chlorine and higher epoxy values, and also in better process safety, as the divalent tin halides and catalyst systems do not polymerise the epihalohydrins. Further, especially when using tin difluoride, the process results in an improved recovery of the tin salt by simple filtration, as tin difluoride is sparingly soluble in organic solvents. In addition, the first reaction step can often be carried out in the melt without a solvent. Furthermore, the reaction products are obtained in great purity. When using tin difluoride, the result obtained in the practice of this invention is all the more surprising, as tin difluoride is not a true Lewis acid.

The glycidyl ethers obtained in the practice of this invention are often used in epoxy resin formulations for modifying specific properties, for example as reactive diluents, flexibilisers, adhesion promoters and the like. These formulations may contain additional optional epoxy resins, such as bisphenol A epoxy resins or epoxy novolaks, and conventional hardeners such as amines, anhydrides, phenols or catalytic hardeners. The formulations find utility in a wide range of application fields, typically as surface-coating resins, dipping resins, impregnating resins, adhesives, sealing compounds, encapsulating compositions and insulating materials. The glycidyl ethers of this invention have excellent resistance to outdoor weathering on account of their aliphatic structure.

The invention is illustrated in more detail by the following Examples in which, unless otherwise stated, parts are by weight.

EXAMPLE 1

1,4-Butanediol diglycidyl ether

A reactor equipped with stirrer, reflux condenser, dropping funnel and thermometer is charged with 180.24 g (2.0 mol) of 1,4-butanediol and 6.27 g (0.04 mol) of tin difluoride and the charge is heated to 130° C. Then, with efficient stirring, 388.6 g (4.20 mol) of epichlorohydrin are added over 2 hours at a temperature of 130°-140° C., the reaction being initially exothermic. After 3 hours at this temperature, the reaction mixture is cooled to 50° C. and to the turbid solution are added 350 ml of xylene, followed by the addition of 30 g of Prolit Rapid ® (filter aid). After stirring for 15 minutes, the suspension is filtered and the filtrate is freed from solvent on a rotary evaporator. Analysis of the tin content of the residual liquid chlorohydrin ether shows that this ether still contains only about 13% of the total amount of tin catalyst, i.e. 87% of the catalyst can be separated by filtration. The liquid chlorohydrin ether (589 g) is heated to 55° C. and 336 g (4.2 mol) of a 50% aqueous solution of sodium hydroxide are added dropwise at this temperature, with efficient stirring, over 30 minutes. After stirring for 2.5 hours at 50°-60° C. and cooling to room temperature, the suspension is filtered and the filtrate washed with xylene. The organic phase of the two-phase clear filtrate is dried over magnesium sulfate and filtered, and the filtrate is freed from solvent on a rotary evaporator under vacuum (bath temperature 50° C.). Yield: 343 g (85% of theory) of colourless 1,4-butanediol diglycidyl ether for which the following analytical values are obtained: epoxy value: 7.81 eq/kg; total chlorine content: 5.5%; hydrolysable chlorine content: 131 ppm.

EXAMPLE 2

Bis(trimethylolpropane) tetraglycidyl ether

A 1.5 liter reactor as used in Example 1 is charged with 250.13 g (1 mol) of bis(trimethylolpropane) [ex Perstorp Chemicals; CH$_3$CH$_2$C(CH$_2$OH)$_2$—CH$_2$OCH$_2$C(CH$_2$OH)$_2$—CH$_2$CH$_3$], and the charge is heated to 120° C. to form a melt which is freed from any water formed by applying a vacuum of c. 30 mbar for 15 minutes. Then 3.13 g (0.02 mol) of finely powdered tin difluoride are added, followed by the addition of 407 g (4.4 mol) of epichlorohydrin at a rate of 3 ml/min with efficient stirring, such that the temperature in the reactor remains at 120°-125° C. The reaction is initially exothermic, but later heating must be effected with an oil bath (bath temperature 130° C.). After this addition, another 1.57 g (0.01 mol) of tin difluoride are added and the reaction mixture is stirred for 6 hours at 120°-125° C. Excess epichlorohydrin is removed from the reactor by distillation under a water jet vacuum (amount of distillate: 52.75 g), then 200 g of isobutyl methyl ketone and 20 g of Prolit Rapid ® are added to the reaction mixture, which is stirred for 30 minutes at room temperature and then while cooling with an ice bath. The reaction mixture is filtered and the residue is washed with 100 g of isobutyl methyl ketone. Analysis of the tin content shows that the filtrate (874 g) contains about 1.75 g of tin, i.e. 50% of the catalyst can be separated by filtration.

The filtrate (epichlorohydrin ether) is heated to 50°-60° C. and, at this temperature, 340 g (4.25 mol) of a 50% aqueous solution of sodium hydroxide are added dropwise over 1 hour with efficient stirring. The reaction is allowed to continue for 2.5 hours at 55°-60° C., then the suspension is filtered and the two-phase filtrate is separated in a separating funnel and the aqueous phase is extracted once more with 250 g of isobutyl methyl ketone. The combined organic phases are neutralised by extraction with a 10% solution of potassium dihydrogen phosphate and dried over magnesium sulfate, filtered, and the solvent is removed on a rotary evaporator. The crude product (457 g) is dried under vacuum (<2000 Pa or 20 mbar), giving 428.32 g (90.3%, based on bistrimethylolpropane) of colourless liquid bis(trimethylolpropane) tetraglycidyl ether for which the following analytical values are obtained: epoxy value: 6.35 eq/kg (75% of theory): chlorine content: 4.10%; hydrolysable chlorine content: 7000 ppm; viscosity at 25° C.: 650 mPa.s; average molecular weight Mn (gel permeation chromatography GPC): 532 (styrene calibration).

EXAMPLE 3

Trimethylolpropane triglycidyl ether

In accordance with the procedure of Example 2, 134.18 g (1 mol) of trimethylolpropane of formula CH$_3$CH$_2$C(CH$_2$OH)$_3$, 3.13 g (0.03 mol) of tin difluoride, 305.25 g (3.3 mol) of epichlorohydrin and 252 g of a 50% solution of sodium hydroxide (3.15 mol) are reacted. 60% of the amount of catalyst can be recovered by filtration in the chlorohydrin step.

Yield: 281.7 g of colourless liquid trimethylolpropane triglycidyl ether for which the following analytical values are obtained: epoxy value: 6.96 eq/kg; viscosity at 25° C.: 140 mPa.s; total chlorine content: 7.8%; hydrolysable chlorine content: 2.3%; average molecular weight Mn (GPC): 398.

EXAMPLE 4

Sorbitol glycidyl ether

A 750 ml reactor equipped with reflux condenser, thermometer, stirrer and metering device for epichlorohydrin is charged with 72.9 g (0.4 mol) of sorbitol and 1.25 g (0.008 mol) of tin difluoride in 88.5 g (0.957 mol) of epichlorohydrin, and the charge is heated to 110° C. Then, with stirring, 132.1 g (1.429 mol) of epichlorohydrin are added at a rate of 1.5 ml/min, while keeping the temperature at 110°-115° C. Stirring is continued for a further 8 hours at 125°–130° C. Excess epichlorohydrin is removed by distillation under a water jet vacuum and the residue is diluted with 441 g of methyl isobutyl ketone. With efficient stirring, 142.4 g (1.78 mol) of a 50% solution of sodium hydroxide are added dropwise over 1 hour and the reaction mixture is kept for another 2 hours at this temperature. The reaction mixture is neutralised by addition of dry ice and filtered, and the organic phase is dried over magnesium sulfate. The solvent is removed on a rotary evaporator and the residue is dried under vacuum (2 hours/60° C.), giving 155.2 g of sorbitol glycidyl ether for which the following analytical values are obtained: epoxy value: 5.5 eq/kg; total chlorine content 15.56%; hydrolysable chlorine content 1.09%; viscosity at 40° C.: 2460 mPa.s; average molecular weight Mn (GPC): 658.

EXAMPLE 5

Tricyclo-[5.2.1.0$^{2.6}$]decane-3(4),8(9)-dimethanol diglycidyl ether

In a 750 ml reactor equipped with reflux condenser, thermometer, stirrer and metering device for epichlorohydrin, 196.29 g (1.0 mol) of tricyclo-[5.2.1.0$^{2.6}$]-decane-3(4),8(9)-dimethanol (TCD Alcohol DM; sold by Hoechst AG) and 3.13 g (0.02 mol) of tin difluoride are heated to 120°–130° C. and, at this temperature, 194.3 g (2.1 mol) of epichlorohydrin are added at a rate of 2.5 ml/min. The reaction mixture is stirred for 12 hours at 125° C. and any epichlorohydrin still present is removed by vacuum distillation. With efficient stirring, 160 g (2.0 mol) of a 50% solution of sodium hydroxide are added and the batch is kept for 2 hours at 30° C. The suspension is filtered and the filtrate is diluted with 500 ml of toluene. The organic phase is extracted with a 10% aqueous solution of potassium dihydrogen phosphate and the extract is dried over magnesium sulfate. The solvent is removed on a rotary evaporator and the residue is dried under vacuum at 100° C., giving 296.3 g (96% of theory), based on the alcohol) of tricyclo-[5.2.1.0$^{2.6}$]-decane-3(4),8(9)-dimethanol diglycidyl ether for which the following analytical values are obtained: epoxy value: 4.67 eq/kg; viscosity at 25° C.: 500 mPa.s; total chlorine content: 5.46%; hydrolysable chlorine content: 2.07%; average molecular weight Mn (GPC): 269.

EXAMPLE 6

1-Hexanol glycidyl ether

A reactor equipped with stirrer, reflux condenser and thermometer is charged with 102.18 g (1.0 mol) of 1-hexanol and 3.14 g (0.02 mol) of powdered tin difluoride, and the charge is heated to 115° C. Then, with efficient stirring, 86.26 ml (1.1 mol) of epichlorohydrin are added over 1 hour. The reaction is allowed to continue for 8 hours, during which time the temperature slowly rises to about 125° C. The reaction mixture is cooled to 55° C. and then, at this temperature, 88 g (1.1 mol) of a 50% aqueous solution of sodium hydroxide are added dropwise with efficient stirring over 30 minutes. After stirring for 6 hours at 55° C. and cooling to room temperature, the suspension is filtered and the filtrate is washed with ethyl acetate. The phases are separated, and the aqueous phase is extracted with 2×100 ml of ethyl acetate. The combined organic phases are neutralised with $CO_2$, dried over magnesium sulfate and filtered. The filtrate is freed from solvent on a rotary evaporator under vacuum (bath temperature 50° C.). Yield: 142.7 g (90.2% of theory) of colourless 1-hexanol glycidyl ether for which the following analytical values are obtained: epoxy value: 5.5 eq/kg (87% of theory); total chlorine content: 3.2% hydrolysable chlorine content: 0.21%.

EXAMPLE 7

Isooctanol glycidyl ether, mixture of isomers

A reactor equipped with stirrer, reflux condenser, dropping funnel and thermometer is charged with 130.23 g (1.0 mol) of isooctanol (mixture of isomers), 3.14 g (0.02 mol) of powdered tin difluoride and 5.28 g (0.02 mol) of 18-crown-6 (crown ether) and the charge is heated to 125° C. The, with efficient stirring, 86.26 ml (1.1 mol) of epichlorohydrin are added over 30 minutes. The reaction is allowed to continue for 20 hours, during which time the temperature rises to about 130° C. The reaction mixture is cooled to 55° C. and then, at this temperature, 88 g (1.1 mol) of a 50% aqueous solution of sodium hydroxide are added dropwise with efficient stirring over 30 minutes. After stirring for 6 hours at 55°–60° C. and cooling to room temperature, the suspension is filtered and the filtrate is washed with ethyl acetate. The phases are separated, and the aqueous phase is extracted with 2×100 ml of ethyl acetate. The combined organic phases are washed with as small an amount of 10% $KH_2PO_4$ solution as possible and then with water until neutral, dried over magnesium sulfate and filtered. The filtrate is freed from solvent on a rotary evaporator under vacuum (bath temperature 50° C.). Yield: 180.7 g (97% of theory) of colourless isooctanol glycidyl ether (mixture of isomers) for which the following analytical values are obtained: epoxy value: 4.71 eq/kg (88% of theory); total chlorine content: 2.7%; hydrolysable chlorine content: 122 ppm.

EXAMPLE 8

Isooctanol glycidyl ether; mixture of isomers

A reactor equipped with stirrer, reflux condenser, dropping funnel and thermometer is charged with 130.23 g (1.0 mol) of isooctanol (mixture of isomers), 4.51 g (0.02 mol) of $SnCl_2.2H_2O$ and 5.28 g (0.02 mol) of 18-crown-6 (crown ether) and the charge is heated to 130° C. Then, with efficient stirring, 86.26 ml (1.1 mol) of epichlorohydrin are added over 30 minutes. The reaction is allowed to continue for 20 hours, during which time the temperature rises to about 135° C. The reaction mixture is cooled to 55° C. and then, at this temperature, 88 g (1.1 mol) of a 50% solution of sodium hydroxide are added dropwise with efficient stirring over 30 minutes. After stirring for 5 hours at 55°–60° C. and cooling to room temperature, the suspension is filtered and the filtrate is washed with ethyl acetate. The phases are separated, and the aqueous phase is extracted with 2×100 ml of ethyl acetate. The combined organic phases are washed with as small an amount of 10% $KH_2PO_4$ solution as possible and then with water until neutral, dried over magnesium sulfate and filtered. The filtrate is freed from solvent on a rotary evaporator under vacuum (bath temperature 50° C.). Yield: 167.4 g (90% of theory) of yellowish isooctanol glycidyl ether (mixture of isomers) for which the following analytical values are obtained: epoxy value: 3.93 eq/kg (73% of theory); total chlorine content: 2.44%; hydrolysable chlorine content: 232 ppm.

EXAMPLE 9

Isooctanol glycidyl ether; mixture of isomers

A reactor of the kind described in Example 8 is charged with 130.23 g (1.0 mol) of isooctanol (mixture of isomers), 5.57 g (0.02 mol) of powdered tin dibromide and 5.28 g (0.02 mol) of 18-crown-6 (crown ether) and the charge is heated to 130° C. Then, with efficient stirring, 86.26 ml (1.1 mol) of epichlorohydrin are added over 30 minutes. The reaction is allowed to continue for 12 hours, during which time the temperature rises to about 135° C. The reaction mixture is cooled to 55° C. and then, at this temperature, 88 g (1.1 mol) of a 50% solution of sodium hydroxide are added dropwise with efficient stirring over 30 minutes. After stirring for 2.5 hours at 55°–60° C. and cooling to room temperature, the suspension is filtered and the filtrate is washed with ethyl acetate. The phases are separated, and the aqueous phase is extracted once with 100 ml of ethyl acetate. The combined organic phases are washed with as small an amount of 10% $KH_2PO_4$ solution as possible and then with water until neutral, dried over magnesium sulfate and filtered. The filtrate is freed from solvent on a rotary evaporator under vacuum (bath temperature 50° C.). Yield: 181.8 g (98% of theory) of yellowish isooctanol glycidyl ether (mixture of isomers) for which the following analytical values are obtained: epoxy value: 3.69 eq/kg (69% of theory); total chlorine content: 3.31%; hydrolysable chlorine content: 750 ppm.

EXAMPLE 10

1,4-Cyclohexane diglycidyl ether

A reactor of the kind described in Example 8 is charged with 116.16 g (1.0 mol) of 1,4-cyclohexanediol and 3.14 g (0.02 mol) of powdered tin difluoride and the charge is heated to 130° C., whereupon the educt melts. Then, with efficient stirring, 152.12 ml (1.94 mol) of epichlorohydrin are added over 30 minutes. The reaction is allowed to continue for 5 hours, during which time the temperature rises to about 135° C. The reaction mixture is cooled to 55° C., 250 ml of toluene are added and, then, at this temperature, 155.2 g (1.94 mol) of a 50% aqueous solution of sodium hydroxide are added dropwise with efficient stirring over 30 minutes. After stirring for 2.5 hours at 55°–60° C. and cooling to room temperature, the suspension is filtered and the filtrate is washed with toluene. The phases are separated, and the aqueous phase is extracted with 5×50 ml of ethyl acetate. The combined organic phases are washed with as small an amount of 10% $KH_2PO_4$ solution as possible and then with water until neutral, dried over magnesium sulfate and filtered. The filtrate is freed from solvent on a rotary evaporator under vacuum (bath temperature 60° C.). Yield: 204.2 g (90% of theory) of yellowish 1,4-cyclohexane diglycidyl ether for which the following analytical values are obtained: epoxy value: 6.0 eq/kg (76% of theory); total chlorine content: 4.3%; hydrolysable chlorine content: 750 ppm.

EXAMPLE 11

Perhydrobisphenol A diglycidyl ether

A reactor of the kind described in Example 8 is charged with 240.4 g (1.0 mol) of perhydrobisphenol A, 3.14 g (0.02 mol) of powdered tin difluoride and 5.28 g (0.02 mol) of 18-crown-6, and the charge is heated to 145° C., whereupon the educt melts. Then, with efficient stirring 152.12 ml (1.94 mol) of epichlorohydrin are added over 30 minutes. The reaction is allowed to continue for 12 hours, then cooled to 55° C., 250 ml of toluene are added and, then, at this temperature, 155.2 g (1.94 mol) of a 50% aqueous solution of sodium hydroxide are added dropwise with efficient stirring over 30 minutes. After stirring for 4.5 hours at 55°–60° C. and cooling to room temperature, the suspension is filtered and the filtrate is washed with toluene. The phases are separated, and the aqueous phase is extracted with 2×100 ml of ethyl acetate. The combined organic phases are washed with a small an amount of 10% $KH_2PO_4$ solution as possible and then with water until neutral, dried over magnesium sulfate and filtered. The filtrate is freed from solvent on a rotary evaporator under vacuum (bath temperature 70° C.). Yield: 330.8 g (94% of theory) of yellowish perhydrobisphenol A diglycidyl ether for which the following analytical values are obtained: epoxy value: 4.31 eq/kg (76% of theory); total chlorine content: 2.1%; hydrolysable chlorine content: 171 ppm.

What is claimed is:

1. An improved process for the preparation of a glycidyl ether of formula I

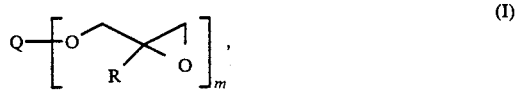

(I)

wherein Q is an aliphatic, cycloaliphatic or araliphatic radical of valency m, R is —H or —$CH_3$, and m is an integer from 1 to 10, by reacting an alcohol of formula Q-$(OH)_m$ with m mol of an epihalohydrin of formula II

(II)

in the presence of a catalyst to the corresponding halohydrin ether, and dehydrohalogenating said halohydrin ether with an alkali metal hydroxide to give a compound of formula I, wherein Q, m and R are as defined above and Hal is halogen, which process comprises using as catalyst a) tin difluoride or b) a divalent tin halide in conjunction with a co-catalyst.

2. A process according to claim 1, wherein the epihalohydrin is selected from epibromohydrin and epichlorohydrin.

3. A process according to claim 2, wherein the epihalohydrin is epichlorohydrin.

4. A process according to claim 1, wherein from 0.8 to 1.3 mol of epihalohydrin of formula II is used per hydroxyl group according to the formula Q-$(OH)_m$.

5. A process according to claim 1, wherein the divalent tin halide is selected from the group consisting of tin dichloride, tin dibromide and tin difluoride.

6. A process according to claim 1, wherein tin difluoride is used as sole catalyst.

7. A process according to claim 1, wherein the tin halide catalyst is used in a concentration of 0.001 to 0.5 mol per mol of alcohol of formula Q-$(OH)_m$.

8. A process according to claim 1, wherein a crown ether or a poly(alkylene oxide) dialkyl ether is used as co-catalyst.

9. A process according to claim 1, wherein m in formula I is an integer from 1 to 6.

10. A process according to claim 1, wherein Q is a saturated aliphatic or cycloaliphatic radical.

11. A process according to claim 1, wherein an aliphatic radical Q is a saturated alkyl radical.

12. A process according to claim 1, wherein the compound of formula Q-(OH)$_m$ is selected from primary or secondary monofunctional (m=1) or polyfunctional alcohols, wherein m is an integer from 2 to 6.

13. A process according to claim 1, wherein Q in formula Q-(OH)$_m$ is a polyfunctional radical containing up to 30 carbon atoms, wherein m is an integer from 2 to 6.

14. A process according to claim 1, wherein the dehydrohalogenation of the halohydrin ether to the glycidyl ether is carried out with the aid of sodium hydroxide.

* * * * *